(12) United States Patent
Zhang et al.

(10) Patent No.: US 8,163,470 B2
(45) Date of Patent: Apr. 24, 2012

(54) SIMULATED 5-PART DIFFERENTIAL LEUKOCYTE GRANULES, THE METHOD FOR PREPARING THE SAME AND CONTROL PRODUCTS AND CALIBRATORS COMPRISING THE SAME

(75) Inventors: Hui Zhang, Shenzhen (CN); Lu Wang, Shenzhen (CN); Zuyue Xu, Shenzhen (CN); Mulong Liu, Shenzhen (CN); Li Zhang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 738 days.

(21) Appl. No.: 12/274,070

(22) Filed: Nov. 19, 2008

(65) Prior Publication Data

US 2009/0258338 A1    Oct. 15, 2009

(30) Foreign Application Priority Data

Apr. 15, 2008   (CN) .......................... 2008 1 0066640

(51) Int. Cl.
*A01N 1/02* (2006.01)
*C12N 5/00* (2006.01)
*C12N 5/02* (2006.01)

(52) U.S. Cl. ............................................. 435/2; 435/375

(58) Field of Classification Search ............... 435/2, 375
See application file for complete search history.

(56) References Cited

U.S. PATENT DOCUMENTS

| | | | |
|---|---|---|---|
| 2,890,120 A * | 6/1959 | Makower ...................... | 426/269 |
| 4,704,364 A | 11/1987 | Carver et al. | |
| 5,262,327 A | 11/1993 | Ryan | |
| 5,270,208 A | 12/1993 | Ryan | |
| 5,320,964 A | 6/1994 | Young et al. | |
| 5,512,485 A * | 4/1996 | Young et al. .................... | 436/10 |
| 5,529,933 A | 6/1996 | Young et al. | |
| 5,672,474 A | 9/1997 | Ryan | |
| 5,677,145 A | 10/1997 | Ryan | |
| 5,731,205 A | 3/1998 | Ryan | |
| 5,758,790 A | 6/1998 | Ewing, Jr. | |
| 5,981,282 A | 11/1999 | Ryan | |
| 6,187,590 B1 | 2/2001 | Kim et al. | |
| 6,200,500 B1 | 3/2001 | Ryan | |
| 6,221,668 B1 | 4/2001 | Ryan et al. | |
| 6,399,388 B1 | 6/2002 | Ryan et al. | |
| 6,403,377 B1 | 6/2002 | Ryan et al. | |
| 6,406,915 B2 | 6/2002 | Ryan et al. | |
| 6,514,763 B2 | 2/2003 | Carver et al. | |
| 6,569,682 B2 | 5/2003 | Elliott et al. | |
| 6,762,055 B2 | 7/2004 | Carver | |
| 2003/0104629 A1 | 6/2003 | Ryan | |
| 2005/0227359 A1 | 10/2005 | Ortiz et al. | |

FOREIGN PATENT DOCUMENTS

CN    1891815 A    1/2007
CN    1891816 A    1/2007

OTHER PUBLICATIONS

Jensen et al., Nitrite disrupts multiple physiological functions in aquatic animals, Comparative Biochemistry and Physiology Part A 135: 9-24, 2003.*

Marquezin et al., Spectroscopic characterization of 2-amino-N-hexadecyl-benzamide (AHBA), a new fluorescence probe for membranes, Biophysical Chemistry 124: 125-133, 2006.*

* cited by examiner

*Primary Examiner* — Wu-Cheng Winston Shen
(74) *Attorney, Agent, or Firm* — Kory D. Christensen; Stoel Rives LLP (57) ABSTRACT

A method for preparing five-part differential leukocyte analogs from red blood cells includes selecting appropriate red blood cells; treating the red blood cells with a multi-functional reagent system for maintenance of a structural integrity of the membranes of the red blood cells and synchronous adjustment of cell volume, morphology and inclusions; subjecting the treated red blood cells to an intensified fixation; and washing the treated cells for preservation. The present disclosure also relates to leukocyte analogs prepared by the above method, a reagent system used for preparing the analogs, and a quality control and a calibrator including the analogs for use in a hematology analyzer.

12 Claims, 5 Drawing Sheets

DIFF

SIMULATED 5-PART DIFFERENTIAL LEUKOCYTE GRANULES, THE METHOD FOR PREPARING THE SAME AND CONTROL PRODUCTS AND CALIBRATORS COMPRISING THE SAME

RELATED APPLICATIONS

This application claims priority to Chinese Patent Application No. 200810066640.7, filed Apr. 15, 2008, for "SIMULATED 5-PART DIFFERENTIAL LEUKOCYTE GRANULES, THE METHOD FOR PREPARING THE SAME AND CONTROL PRODUCTS AND CALIBRATORS COMPRISING THE SAME," the disclosure of which is fully incorporated herein by reference.

TECHNICAL FIELD

The present disclosure relates to the field of hematology, more specifically, to five-part differential leukocyte analogs prepared using red blood cells, methods for preparing the same, and a quality control and a calibrator comprising the same.

BRIEF SUMMARY

Methods and systems for preparing five-part differential leukocyte analogs from red blood cells are disclosed.

DETAILED DESCRIPTION

Figure 1:
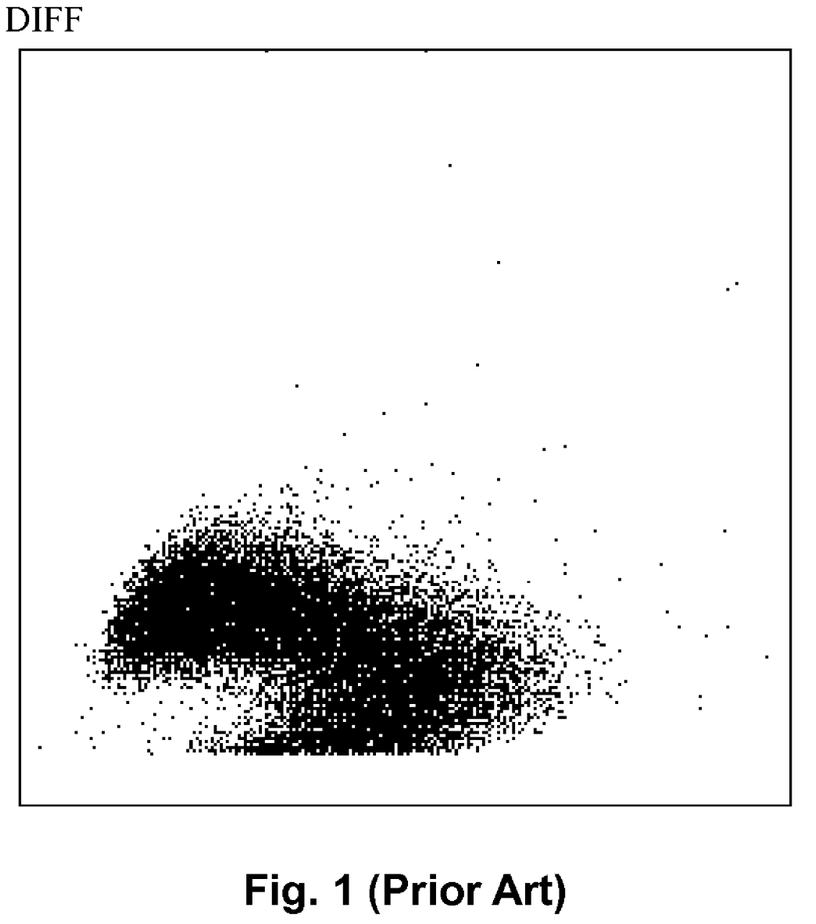
FIG. 1 is a scattergram for leukocyte analogs prepared from red blood cells for use in an impedance principle (see U.S. Pat. No. 4,704,364 for the preparation method), as detected on a white blood cell differential detection channel, i.e. four-part differential WBC/DIFF channel, of five-part differential hematology analyzer BC-5500 (Mindray Bio-Medical Electronics Co., Ltd, Shenzhen, China).

The quality controls and calibrators for five-part differential hematology analyzers using optical detection technology include leukocyte analogs that differ from those used in the analyzer counterparts based on a impedance-based method (see for example, FIG. 1 of U.S. Pat. No. 4,704,364). The leukocyte analogs for five-part differential hematology analyzers usually need to have a relatively good volume distribution, as well as a good complexity distribution in cell optics. Some analogs further need to have specific fluorescent properties. The biconcave shape or spindle shape of human or animal red blood cells can result in failure to exhibit concentrated distribution of optic properties upon optical detection of the cells, following their direct fixation on a five-part differential hematology analyzer. Therefore, conventional analogs meeting the requirements on stable volume and light scatter are prepared using white blood cells (leukocytes) from the blood of human or other animals by purification of the cells from the blood followed by fixation thereof. Unfortunately, this conventional strategy poses a relative high requirement on materials, cost and processes as well. On the other hand, analogs prepared using red blood cells are rare, and, as discussed herein, conventional processes of preparation may suffer from some drawbacks.

Existing methods for preparing human or animal white blood cells into five-part differential leukocyte analogs involve the steps of hemolysis, fixation and washing, etc. Generally, red blood cells are first removed, and then white blood cells are separated. The separated cells are subjected to fixation or stepwise fixation, and subsequently washed. The washed cells are preserved, e.g., in a preserving fluid comprising lipoprotein, such that the leukocyte analogs have properties closer to those of true white blood cells. See for example, U.S. Pat. Nos. 6,406,915, 6,403,377, 6,399,388, 6,221,668, 6,200,500, 5,981,282, 5,731,205, 5,677,145, 5,672,474, 5,270,208, 5,262,327, 6,762,055, 6,514,763, 6,187,590 and 5,858,790.

However, the use of white blood cells for the preparation of analogs may suffer from certain disadvantages, of which the following two are prominent:

(1) Difficulty in obtaining white blood cells, which can lead to increased cost and complicated processes. The processes for obtaining white blood cells free of red blood cells are rather complex, since the concentration of white blood cells in human and animal blood is 100 to 1,000 times lower than that of red blood cells. Furthermore, the use of a lytic reagent may lead to undesirable changes in the properties of white blood cells such that purified white blood cells cannot be evaluated by the physiological state of the white blood cells. In addition, the processes for removing red blood cells are rather complex such that it is not easy to achieve satisfactory results even with the use of expensive cell separation fluid. This can pose a problem to the cost in and the product of the calibrator and quality control for five-part differential hematology analyzers.

(2) Inapplicability to use intensified aldehyde fixation techniques, which can lead to instability of the products.

White blood cells differ considerably from red blood cells in their cell membrane surface properties so that they quite readily manifest themselves in an aggregated state. This is more pronounced in the process of fixation with aldehydes. Hence, to lower the impact of aggregation on cell distribution, the leukocyte analogs, in contrast with red blood cells, usually cannot be subjected to treatment with a higher concentration of aldehydes at an elevated temperature for a prolonged period for fixation. The leukocyte analogs thus prepared, as a result, may suffer from a varying degree of decrease in stability.

Methods for preparing five-part differential leukocyte analogs using red blood cells generally comprise expanding red blood cells to release hemoglobin, and then fixing the cells. See for example U.S. Pat. No. 5,512,485. The leukocyte analogs prepared using such a method are suitable for use with VCS (i.e., detection of Volume, Conductivity and light Scatter) technology.

Although, conventionally, the use of red blood cells omits the separation of white blood cells, thereby simplifying part of the processes, it also has some shortcomings, of which the following two are prominent:

(1) Red blood cells have a morphology and structure quite different from white blood cells such that the analogs prepared from them generally have a lower degree of simulation than those prepared from white blood cells and thus will need a series of adjustments.

(2) Conventional treatments of red blood cells are relatively complicated in that adjustment of volume (including pretreatment for stability prior to the adjustment), adjustment of hemoglobin content and long-time, low-temperature fixation are required. These complicated treatments, particularly the expansion of the volume, significantly reduce the membrane integrity of red blood cells, leading to problems associated with lower stability and reduced yield of finished product. Moreover, the undue burden of treatment poses greater challenges to the process as a whole and may, to a certain degree, impair the reproducibility of products, which will lower the practicability and controllability of the processes.

In view of the problems associated with conventional technology discussed herein, the present disclosure proposes a simple method for preparing leukocyte analogs from red blood cells for use in calibrator and quality control for five-part differential hematology analyzers, and develops a reagent system for one-step adjustment of the volume, morphology and inclusions of red blood cells.

One embodiment of the present disclosure involves a method for preparing leukocyte analogs from animal red blood cells, the method including the steps of:

(1) Selecting red blood cells derived from suitable species based on different leukocyte subpopulations to be simulated.

(2) Adjusting the properties of the red blood cells with a reagent system including the following components: (i) a morphology adjusting component, which is an erythrocyte sphering agent comprising a surfactant as an active ingredient and optionally a weak acid, wherein the concentration of the surfactant is such that it does not disrupt the red blood cells and does not lead to leakage of hemoglobin out of the cells, for example the surfactant concentration being between 0.005%-0.5%; (ii) an inclusion adjusting component, which is a hemoglobin oxidizing agent or reducing agent, (iii) a volume adjusting component, which is an osmotic regulator for fine adjustment of osmolality, optionally selected from at least one of the following: sodium chloride, monobasic sodium phosphate, potassium chloride and sodium citrate; and (iv) a cell membrane strengthening component, which is an organic aldehyde.

(3) Fixing the treated red blood cells so that they are resistant to the action of a hemolytic agent.

(4) Washing, concentrating and preserving the fixed red blood cells.

In the above embodiment, the red blood cells from step (2) may be subjected to a short-time, high-intensity fixation, e.g. fixation with 0.5% glutaraldehyde for about 2 hours. The surfactant may be a cationic, anionic, nonionic and/or a zwitterionic surfactant and the weak acid may be acetic acid. The oxidizing agent or reducing agent may be selected from at least one of the following: sodium nitrite, potassium dichromate, potassium permanganate, hydrogen peroxide and sodium sulphite. The cell membrane strengthening component may be an aldehyde compound selected from paraformaldehyde, formaldehyde, pyruvaldehyde, oxalaldehyde and glutaraldehyde, or a mixture thereof. In one embodiment, the reagent system used in step (2) comprises: (i) 0.005%-0.5% (w/v) sodium dodecyl sulphonate, or 0.005%-0.5% (w/v) hexadecyl trimethyl ammonium chloride, based on the final concentration, and/or (ii) 0.1%-1% (w/v) sodium nitrite, 0.1%-2% (w/v) potassium dichromate, 0.05%-2% (w/v) potassium permanganate, 0.05%-5% (v/v) hydrogen peroxide, or 0.1%-2% (w/v) sodium sulphite, based on the final concentration, and/or (iii) 0.75-2% (w/v) sodium chloride solution, 1%-3% (w/v) monobasic sodium phosphate solution, 0.75-2% (w/v) potassium chloride solution, or 1%-4% (w/v) sodium citrate solution, based on the final concentration, and/or (iv) 0.01%-0.1% (v/v) glutaraldehyde, 0.05%-0.5% (v/v) formaldehyde, 0.05-0.2% (v/v) mixed aldehydes of formaldehyde and glutaraldehyde in a volume ratio of 3:1-40:1, 0.05%-0.5% (v/v) pyruvaldehyde, or 0.01%-0.1% (v/v) paraformaldehyde, based on the final concentration.

Another embodiment involves a reagent system useful for preparing leukocyte analogs from animal red blood cells, comprising: (i) a morphology adjusting component, which is a red blood cell sphering agent having surfactants as active ingredients and optionally including weak acids such as acetic acid, wherein the concentration of the surfactants is such that it does not disrupt the red blood cells and does not lead to leakage of hemoglobin out of the cells, such as between 0.005%-0.5%; (ii) an inclusion adjusting component, which is a hemoglobin oxidizing agent or a hemoglobin reducing agent, and optionally selected from at least one of the following: sodium nitrite, potassium dichromate, potassium permanganate, hydrogen peroxide and sodium sulphite; (iii) a volume adjusting component, which is an osmotic regulator used for fine adjustment of osmolality; and (iv) a cell membrane strengthening component, which is organic aldehydes, optionally selected from paraformaldehyde, formaldehyde, pyruvaldehyde, oxalaldehyde and glutaraldehyde, or a mixture of these fixing agents.

The present disclosure also involves quality control and a calibrator for hematology analyzers, both of which comprise the leukocyte analogs prepared by the above method.

Highly stable leukocyte analogs were obtained through many endeavors, including study on red blood cells from many species and on the structural characteristics of red blood cells per se, intensive investigation on the possibility of synchronization of multiple treatment reactions, and strict test on compatibility of each of the reactions in the same system. These efforts balance the maintenance of the structural integrity of red blood cells and simulation of the optical properties of white blood cells, and simplify the fixation process while intensifying the strength of the analogs. The particular features of one embodiment are as follows:

(1) Synchronously adjusting the morphology and inclusions of red blood cells while maintaining the structural integrity of the cells: If the red blood cells are kept structurally integral, a relatively light burden is placed upon the fixation process, thus allowing for easy control and less interference. Moreover, intact red blood cells maintain higher structural stability after being fixed. Therefore the process schemes devised in the present disclosure pursue a maximum maintenance of the structural integrity of red blood cells by all means.

In light of the principle of optical detection by hematology analyzers, red blood cells typically scatter more light than white blood cells mainly in that red blood cells do not take a spherical shape such that the red blood cells will pass the optical detection region at various postures (angles), leading to more light being scattered. Therefore, an increased consistency in light scattering properties entails spheroidization of red blood cells without undue treatments.

During hematology analysis, it was found that to lessen influence on and improve stability of the intracellular hemoglobin, direct and simple chemical modifications such as oxidation and reduction of intracellular hemoglobin, e.g., oxidation of $Fe^{2+}$ in hemoglobin to $Fe^{3+}$, are helpful. This enhances the stability of hemoglobin during prolonged storage. By retaining hemoglobin inside the red blood cells to prevent it from leakage, the structure of cell membranes is less likely to be destroyed, thus maintaining the structure of cells and enhancing the stability of the cell particles.

The membranes of red blood cells retain a rather high elasticity after the cells are globularized, such that the cells tend to restore their natural morphology in the absence of spheroidization environments. Therefore, an organic aldehyde in a suitable concentration may be added to achieve a preliminary intensification of the cell membranes. Accordingly, the above three major adjustments are simultaneously achieved by one step simply using a reagent system (one-step reagent system). In spite of an increased technological difficulty, this avoids unknown risks in the transitional stages between various steps of adjustment, and increases the degree of standardization of the processes.

(2) Intensifying the cell membranes and increasing the cell stability using intensified fixation conditions: According to one exemplary method, the structure of red blood cells maintains integral, and hemoglobin is trapped inside the cells on fixation. This imposes less influence on fixation, and makes it possible to use an increased concentration of a fixative. Therefore, a short-time, a high-intensity fixation treatment can be performed using a higher concentration of a fixative or a mixture of fixatives with the benefit of both simplifying the fixation processes and achieving a more stable effect.

(3) Making use of red blood cells from various species to meet the distribution requirements of instrumentation: In order to maintain the integrity of red blood cells, treatment methods such as regulation of osmolality, and chemical and physical treatments are generally used. However, as one embodiment of the disclosed method does not seriously disrupt the cellular structure and it minimizes the possibility of hemoglobin leakage, the above method for adjusting the volume of red blood cells is restricted and the adjustable volume range of the cells is narrow. With a view for obtaining more distribution characteristics for instrumentation, it is recommended to increase the variety of red blood cells. For example, porcine red blood cells can be used to prepare leukocyte analogs with similar distribution characteristics to lymphocytes, elephant or loach red blood cells can be used to prepare leukocyte analogs approximated to eosinophils and neutrophils, and avian red blood cells can be used to prepare analogs for monocytes, to name but a few. More biological species can be covered depending on the applicability of instrumentation in order to make full use of the cellular properties of the organism per se so as to make full play of instrumentation.

In summary, this exemplary method makes it possible to markedly simplify the entire process, lower cost and prepare leukocyte analogs that are stable enough to be used in five-part differential calibrator and quality control.

The preparation of five-part differential leukocyte analogs from red blood cells mainly includes the following steps: (1) selecting red blood cells from a suitable species based on different distribution requirements for the analogs to be prepared; (2) adjusting the properties of red blood cells, including fine adjusting of cell volume (if necessary), and sphering in morphology, to reduce optical complexity distribution, modify the optical properties of inclusions, and preliminarily intensify the cell membranes; (3) subjecting the treated red blood cell to a short-time, high-intensity fixation so that they are resistant to the action of lytic reagents; (4) stringently washing, concentrating and preserving the fixed red blood cells; and; (5) adding red blood cell and platelet components to prepare multi-parameter calibrator and quality control if necessary.

The exemplary method and the reagents and materials used are further illustrated hereinafter.

I. Preparation of the Materials

1. Red Blood Cells. The red blood cells used in the method disclosed are those from a suitable animal and can be suitably selected dependent on leucocytes to be simulated. The term "animal" as used herein includes human, and therefore animal red blood cells include those of fishes, amphibians, reptiles, birds (avians) and mammals, including human. As hereinabove exemplified, porcine red blood cells can be used to prepare leukocyte analogs with similar distribution characteristics to lymphocytes, elephant or loach red blood cells can be used to prepare leukocyte analogs approximated to eosinophils and neutrophils, and avian red blood cells can be used to prepare analogs for monocytes. In addition, as red blood cells account for the overwhelming majority of all blood cells in animal whole blood (including human), there is therefore no need to remove the other components. Put another way, whole blood can be used as a source of red blood cells to prepare leukocyte analogs.

2. One-Step Reagent System. The one-step reagent system disclosed is capable of maintaining the membrane integrity of red blood cells, and simultaneously adjusting cell volume, morphology and inclusions by one single step, which includes the following components:

(A) A Morphology Adjusting Component: This component is an erythrocyte sphering agent including a cationic, anionic, nonionic, and/or zwitterionic surfactant as an active ingredient, such as a conventionally or commercially used lytic reagent, e.g., quaternary ammonium salts, saponins etc., and optionally comprising a weak acid such as acetic acid. The concentration of the surfactant is such that it does not disrupt the red blood cells or lead to the leakage of hemoglobin out of the cells. The criterion for judgment is that it does not make the color of the blood turn from the original bright red color to a dark red color. For example, 0.005%-0.5% (w/v) sodium dodecyl sulphonate or 0.005%-0.5% (w/v) hexadecyl trimethyl ammonium chloride, based on the final concentration, can be used.

(B) An Inclusion Adjusting Component: Any substance known in the art to oxidize or reduce hemoglobin can be used, such as sodium nitrite, potassium dichromate, potassium permanganate, hydrogen peroxide and sodium sulphite, etc. Its concentration can be determined according to technologies known in the art. For example, 0.1%-1% (w/v) sodium nitrite, 0.1%-2% (w/v) potassium dichromate, 0.05%-2% (w/v) potassium permanganate, 0.05%-5% (v/v) hydrogen peroxide, and 0.1%-2% (w/v) sodium sulphite etc., based on final concentration as well, can be used.

(C) A Volume Adjusting Component: In order to reduce the minute differences in volume among the batches of cells, the cell volume can be adjusted by fine adjusting the osmolality with an osmotic regulator. In order to ensure the integrity of cell structure, the fine adjustment of volume is such that the cells are not lysed and hemoglobin does not leak out. The osmotic regulator is well known to those skilled in the art, examples of which are sodium chloride, monobasic sodium phosphate, potassium chloride and sodium citrate, etc. Those skilled in the art may select an osmotic regulator and its concentration used according to the common technological knowledge in the art. For example, use of 0.75-2% (w/v) sodium chloride solution, 1%-3% (w/v) monobasic sodium phosphate solution, 0.75-2% (w/v) potassium chloride solution, or 1%-4% (w/v) sodium citrate solution etc., based on the final concentration, can suitably expand or shrink the cells while maintaining the integrity of cell structure and preventing leakage of hemoglobin and other intracellular components.

(D) A Cell Membrane Strengthening Component: The cell membrane strengthening component may be an organic aldehyde selected from at least one of the following: paraformaldehyde, formaldehyde, pyruvaldehyde, oxalaldehyde, and glutaraldehyde, or a mixture thereof. The concentration suitable for use can be determined depending on the specific aldehyde compound selected. For example, 0.01%-0.1% (v/v) glutaraldehyde, 0.05%-0.5% (v/v) formaldehyde, 0.05-0.2% (v/v) mixed aldehydes of formaldehyde and glutaraldehyde in a volume ratio of 3:1-40:1, 0.05%-0.5% (v/v) pyruvaldehyde, or 0.01%-0.1% (v/v) paraformaldehyde, based on the final concentration, can be used.

3. Fixative. Any fixative useful for fixing red blood cells can be used, including an aldehyde compound such as paraformaldehyde, formaldehyde, pyruvaldehyde, oxalaldehyde, and glutaraldehyde, or a mixture thereof, for example, a mixture of formaldehyde and glutaraldehyde in a volume ratio of 3:1-40:1. The concentration of the fixative can be determined depending on the specific fixative used by reference to conventional fixation methods. As hereinabove stated, the method disclosed reduces interference with the high-concentration aldehyde fixation because the intracellular hemoglobin will not leak out of the cells. Consequently, red blood cells may be fixed with a fixative in a higher concentration for a short period of time, for examples, 0.5%-1% (v/v) glutaraldehyde, 0.5%-1% (v/v) mixed aldehydes (a mixture of formaldehyde and glutaraldehyde in a volume ratio of 3:1-40:1), based on the final concentration.

4. Washing Solution. A conventional isotonic solution can be used, such as isotonic phosphate buffered saline (PBS), physiological saline solution, isotonic glycine solution, and isotonic sodium citrate solution, etc.

5. Preservation Solution. An antiseptically effective preservation solution adapted for preserving cells can be used.

II. Method of Preparation

The method for preparing leukocyte analogs from red blood cells according to the present invention comprises the following steps:

1. Adjustment of cell volume morphology and inclusions: The obtained red blood cells may first be subjected to spheroidization and a treatment directed to hemoglobin. Treatment of hemoglobin can enhance the homogeneity and stability of the optical properties of the red blood cells per se. This is done by suitably diluting the blood with a buffer or saline solution, followed by adding reagents for treatment, which include a surfactant, oxidant, aldehyde, etc. Again, the concentration of the surfactant is such that it does not disrupt the red blood cells or lead to the leakage of hemoglobin out of the cells (that is, it does not make the color of the blood turn from the original bright red color to dark red color). The surfactant is mainly for the purpose of spheroidization and the oxidant is for the purpose oxidizing hemoglobin to stabilize its structure. The aldehyde used in this step of the method is in a relatively low concentration in order to confer the cell membranes with a certain strength so that spheroidization of the red blood cells can be maintained.

The above adjustment can be carried out at room temperature so that the cells are desirably adjusted. In one embodiment, cell populations tremendously different in volume are of different biological origins. It is also applicable to suitably adjust the cell volume at the same time of adjusting the cell morphology and inclusions. One approach is, for example, adjusting osmolality to remove the volume difference due to the diversity of individuals of the same species, which is a relatively small difference, and can be smoothed out by fine adjustment of volume.

2. Intensified fixation. The red blood cell particles so treated are detected on a five-part differential hematology analyzer. If the cells fail to meet the distribution requirement, the above-described treatment is to be properly prolonged. If the treated red blood cell particles are found to meet the distribution requirement and are relatively stable, the adjustment of the cells is basically achieved. Now the cells can be subjected to a further intensified fixation with an aldehyde to increase the stability of the cell particles. The treated red blood cell particles can be fixed using conventional methods.

In addition, as the contents of plasma components are very low, a high concentration of an aldehyde will not result in coagulation of plasma proteins. Also, the intracellular hemoglobin will not leak out of the cells and its interference with the high-concentration aldehyde fixation will be reduced. Thus, a short-time fixation using a high concentration of a fixative is performed. For example, fixation can be performed using 0.5% (v/v) glutaraldehyde (based on the final concentration) at room temperature for about 2 hours. In some cases, the cells may be fixed using mixed aldehydes that combine the benefits of the inherent properties of different aldehydes. For example, the mixture of formaldehyde and glutaraldehyde brings together the penetrating property of formaldehyde and the cross-linking property of glutaraldehyde, conferring a long-term stability on the processed cell particles to meet the requirement of instrumental detection. For example, red blood cells can be fixed using a 0.5% (v/v) 1:10 glutaraldehyde-formaldehyde mixed solution (based on the final concentration) at room temperature for about 2 hours. The leukocyte analogs prepared by fixing the cells with 0.5% (v/v) glutaraldehyde (data not shown) or a 0.5% (v/v) 1:10 mixture of glutaraldehyde and formaldehyde at room temperature for about 2 hours are stable and resistant to the lytic reagents conventionally used in detection.

3. Washing by centrifugation and preservation. The fixed cell particles can be then washed with a physiological saline or other isotonic solutions for many times to remove any residual aldehyde(s), and subsequently preserved at a low temperature in an antiseptically effective preservation solution.

4. Preparation of multi-parameter products. Red blood cells and platelet components may be added as required to prepare multi-parameter calibrator and quality control.

In summary, one embodiment of the present disclosure has the following features: (1) Structurally intact red blood cells are used to prepare leukocyte analogs for use in calibrator and quality control; (2) The red blood cells are treated using a one-step reagent system, so that under the action of this reagent system, the integrity of the cell membranes is maintained, and in the meantime the cell volume, morphology and inclusions are simultaneously adjusted, so that various parameters are more stable to meet the distribution requirement of white blood cells, and the optical complexity is more homogeneous; and (3) An intensified fixation is performed upon the cells subsequent to spheroidization, hemoglobin treatment and preliminary fixation. A preliminary fixation is used during spheroidization and hemoglobin treatment process, and an intensified fixation is performed after the distribution requirement is met.

The present disclosure includes embodiments which may have the following benefits compared to conventional techniques: 1) Abundant raw materials: red blood cells are readily available as their concentration in blood is much higher than that of white blood cells; 2) Simple processes: there is no need to purify white blood cells, which makes the white blood cells less likely to aggregate. Various properties of red blood cells have been simultaneously adjusted in a single step, thus reducing the burden on the processes of red blood cell treatment; 3) Low cost: expensive reagents and equipments are not demanded, thus placing a low requirement on the environment; and 4) Stable products: an intensified fixation is allowed so that the products have a higher stability.

Experiments have shown that the analogs prepared according to the present disclosure have an excellent volume distribution. Hence, the method disclosed is applicable to the calibrator and quality control for impedance-based analyzers. The method is in effect a technology for preparing cell particles compatible with an impedance-based detection.

Red blood cell particles treated with the method disclosed, besides having changed optical detection properties, can be used as a carrier, which can be further modified, e.g., by labeling with a fluorescent substance or a biological substance such as an antigen, antibody etc., to form simulated particles that comply with the principles of fluorescent or immunological detection.

The following examples are illustrative only, intended for those skilled in the art to better understand and practice the present disclosure.

EXAMPLES

Example 1

Simulating Lymphocytes with Human Red Blood Cells

1. The treatment reagent was prepared as follows: To 195 ml of distilled water was added 1.5 g of sodium chloride, 1 g of sodium nitrite, 100 µl of 1% (w/v) sodium hexadecyl sulphonate and 100 µl of 25% (v/v) glutaraldehyde.

2. The above treatment reagent was mixed with 5 ml of anticoagulant human whole blood, and the mixture was left still at room temperature for about 30 minutes.

3. The mixture was analyzed on the analyzer BC5500, and then a decision was made, based on different distribution requirements, as to whether an intensified fixation was to begin.

4. When the reaction mixture was determined to meet the distribution requirement (i.e., when the DIFF image showed that the dots were located in the region for lymphocytes), a 0.5% (v/v) 1:10 mixture of glutaraldehyde and formaldehyde (based on the final concentration) was added to the reaction mixture and remained still at room temperature for 2 hours.

5. The new mixture was then analyzed using the analyzer to observe changes in cell count and distribution.

6. After related requirements were met (i.e., the cell count and the image were relative stable), the reaction mixture was washed with physiological saline by centrifugation for three times to remove residual aldehydes, then concentrated and preserved in a preservation solution at a low temperature. See FIG. 3 for the DIFF image resultant from analysis of the BC5500 analyzer.

Example 2

Simulating Neutrophils with Elephant Red Blood Cells

1. The treatment reagent was prepared as follows: To 195 ml of purified water were added 1.5 g of sodium chloride, 1 g of sodium nitrite, 100 µl of 1% (w/v) sodium hexadecyl sulphonate and 100 µl of 25% (v/v) glutaraldehyde.

2. The above treatment reagent was mixed with 5 ml of anticoagulant elephant whole blood, and the mixture was let still at room temperature for about 30 minutes.

3. The mixture was analyzed using the analyzer, and a decision was then made, based on different distribution requirements, as to whether an intensified fixation was to begin.

4. When the reaction mixture was determined to meet the desired distribution requirement (i.e., when the DIFF image showed that the dots were located in the region for neutrophils), a 0.5% (v/v) 1:10 mixture of glutaraldehyde and formaldehyde (based on the final concentration) was added to the reaction mixture and let still at room temperature for 2 hours.

5. The new reaction mixture was then analyzed by the analyzer to observe changes in cell count and distribution.

6. After related requirements were met (i.e., the cell count and the image were relatively stable), the reaction mixture was washed with physiological saline by centrifugation for three times to remove residual aldehydes, then concentrated and preserved in a preservation solution at low temperature. See FIG. 4 for the DIFF image resultant from the analysis of the BC5500 analyzer.

Figure 5:
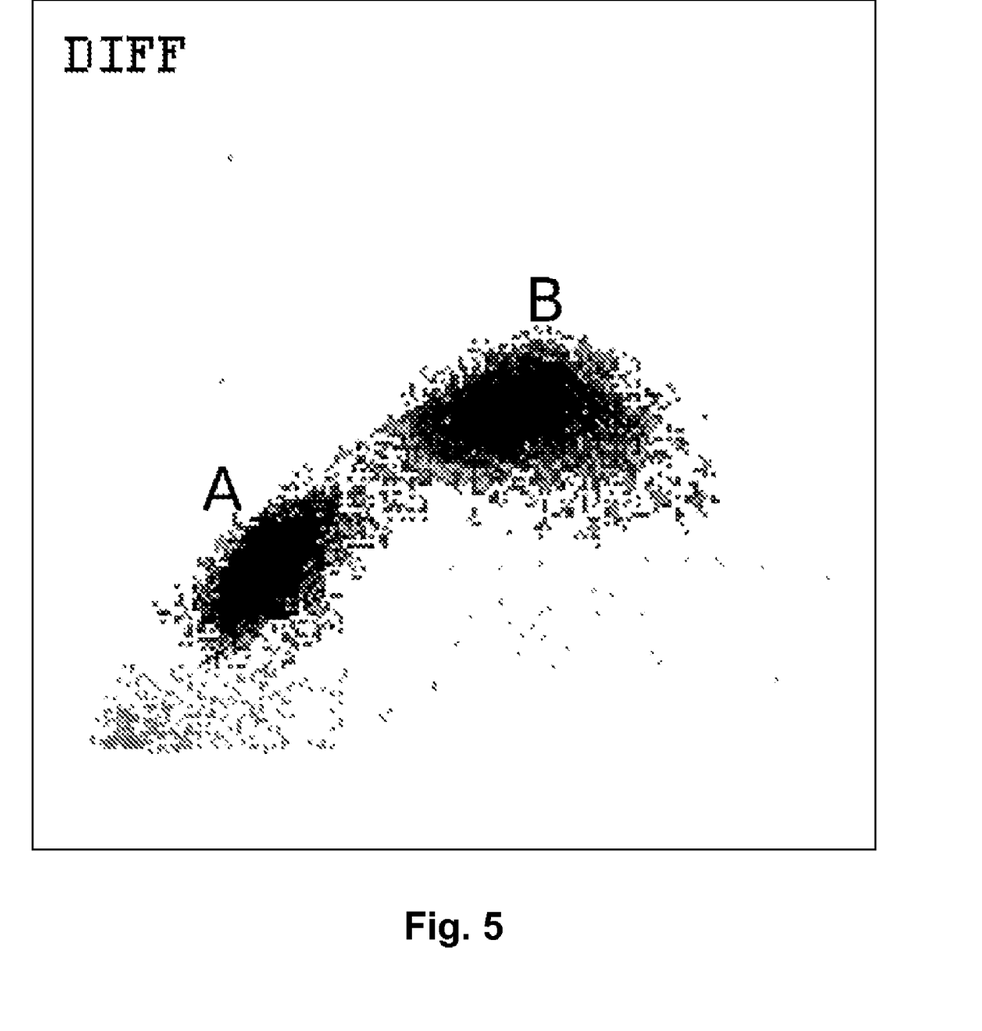
FIG. 5 is a scattergram of mixed red blood cells treated using the two different methods, wherein portion (A) of the DIFF image shows the distribution of lymphocyte analogs prepared from human red blood cells using one-step simulation technology disclosed, and portion (B) of the DIFF image shows the distribution of neutrophil analogs prepared from elephant red blood cells using one-step simulation technology disclosed.

The leukocyte analogs prepared in Examples 1 and 2 were combined and analyzed on the BC5500 analyzer to finally obtain a DIFF image as shown in FIG. 5.

Results

Figure 2:
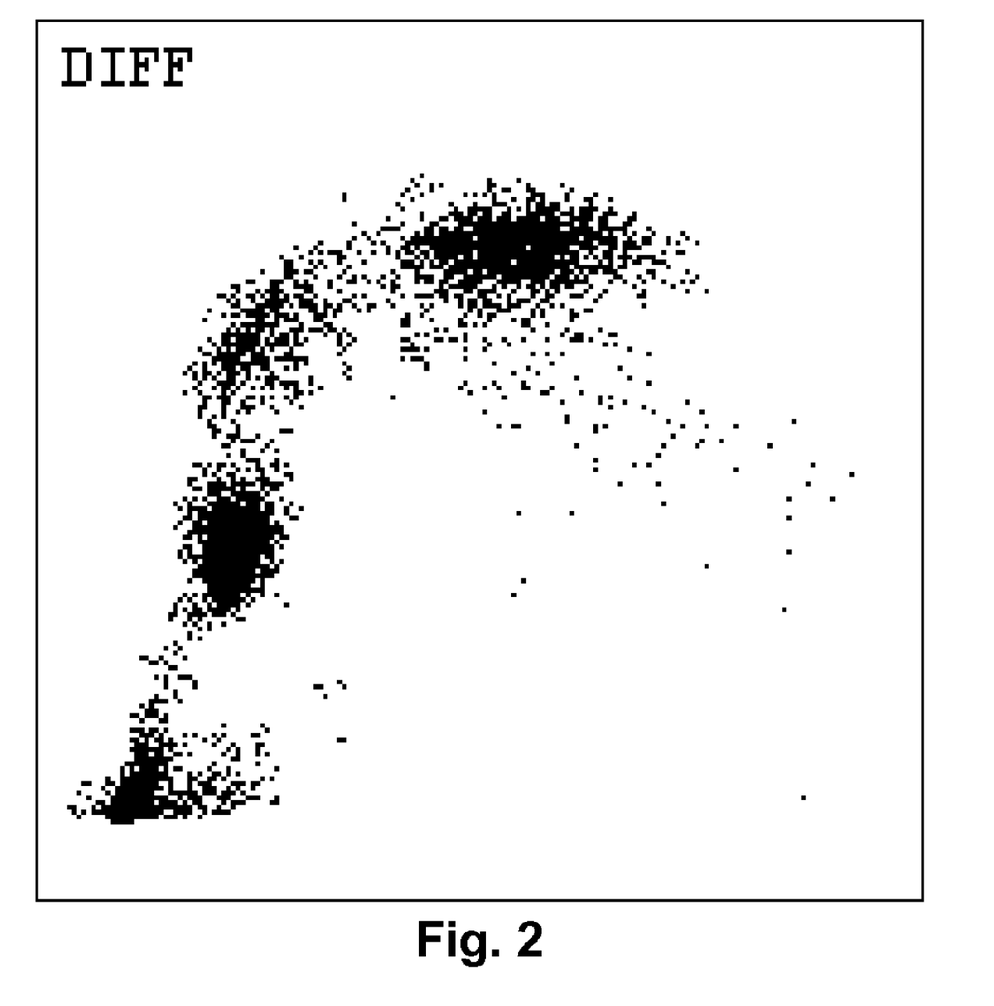
FIG. 2 is a scattergram illustrating fresh human whole blood in the DIFF channel of a five-part differential hematology analyzer BC-5500.

FIG. 1 shows a scattergram of leukocyte analog prepared from red blood cells for use in an impedance principle in the DIFF channel of a four-part differential hematology analyzer. As shown in FIG. 1, such an analog shows no sign of clustering, and its scattergram distribution is different from that of any kind of human white blood cells (see FIG. 2). Therefore, such an analog can not be used to monitor the counting and differentiation by the analyzer. Therefore, conventional technologies for preparing quality control fail to meet the current need of a five-part differential analyzer.

Figure 3:
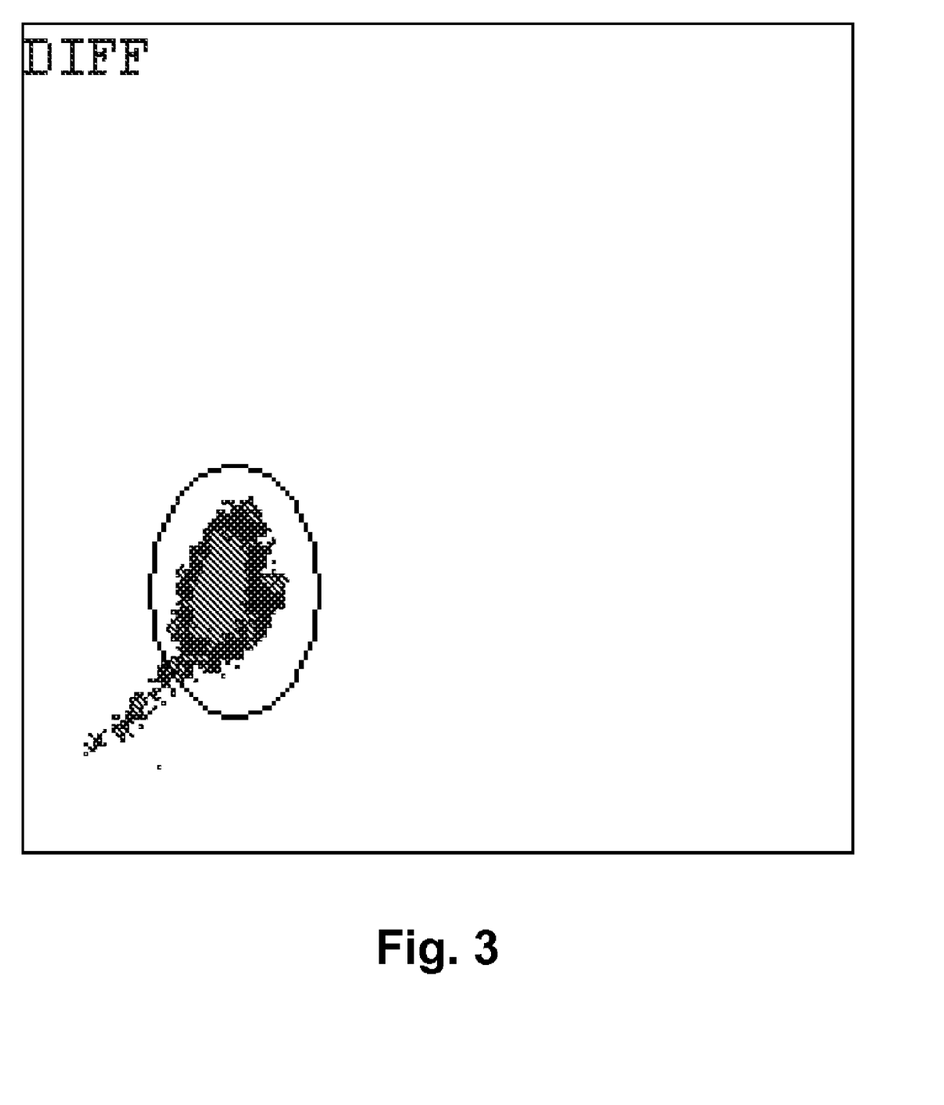
FIG. 3 is a DIFF image in which the portion inside the ellipse shows the distribution of lymphocyte analogs prepared from human red blood cells using one-step simulation technology disclosed. It can be seen that the cells have good clustering and there are few fragments and scattered particles, so basic requirements for the quality control of instrumentation have been met.
Figure 4:
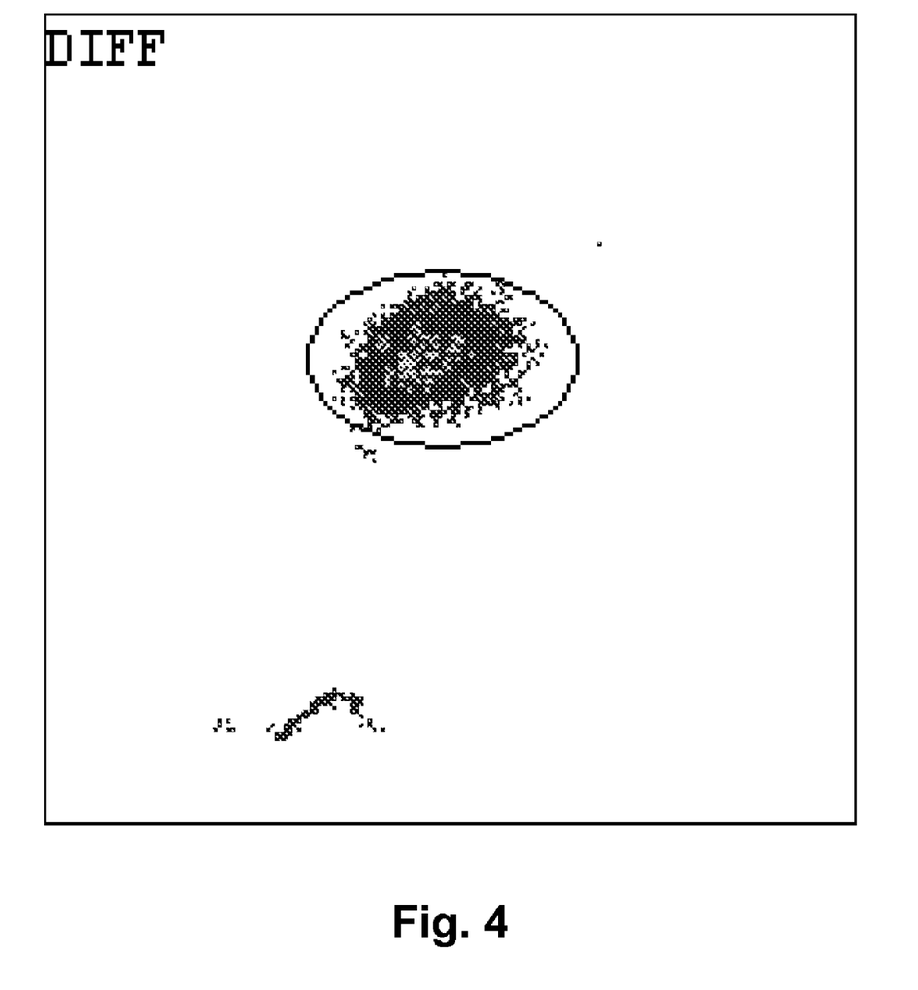
FIG. 4 is a DIFF image in which the portion inside the ellipse shows the distribution of neutrophil analogs prepared from elephant red blood cells using one-step simulation technology disclosed. It can be seen that the cells have good clustering and there are few fragments and scattered particles, so basic requirements for the quality control of instrumentation have been met.

In contrast, it can be seen from FIG. 3-FIG. 5 that the leukocyte analogs prepared by one embodiment of a method of the present disclosure (one-step method) have good clustering with few fragments and scattered particles. The light scatter properties of true white blood cells can be well simulated. Therefore, basic requirements for the quality control of instrumentation have been met.

Moreover, similar results were obtained with lymphocyte analogs prepared from porcine red blood cells (data not shown).

In addition, stability tests on the analogs prepared (data not shown) showed that their shelf-life stability and in-use stability and other indices have reached the levels of their foreign counterparts. Such analogs were stable for over 120 days when hermetically preserved at 2-8° C.

Although the present disclosure has been described with reference to the particular embodiments as described above, one skilled in the art will recognize that the present invention is not limited to these particular embodiments. Modifications and improvements can be made to the particular embodiments without departing from the spirit and scope of the present invention, as claimed. These equivalent embodiments shall be construed to fall into the scope of the present invention.

What is claimed is:

1. A method for preparing leukocyte analogs from animal red blood cells, comprising the steps of:
   (1) selecting red blood cells derived from suitable species based on different leukocyte subpopulations to be simulated;
   (2) adjusting the properties of the red blood cells while maintaining the structural integrity of the red blood cells by treating them with a reagent system comprising the following components:
      (i) a morphology adjusting component, comprising an erythrocyte sphering agent comprising a surfactant as an active ingredient and optionally a weak acid, wherein the concentration of the surfactant is such that it does not disrupt the red blood cells and does not lead to leakage of hemoglobin out of the cells,
      (ii) an inclusion adjusting component, which is a hemoglobin oxidizing agent or reducing agent,
      (iii) a volume adjusting component, which is an osmotic regulator for fine adjustment of osmolality, and
      (iv) a cell membrane strengthening component, which is an organic aldehyde;
   (3) fixing the treated red blood cells after adjusting the properties so that they are resistant to the action of a hemolytic agent; and
   (4) washing, concentrating and preserving the fixed red blood cells, wherein the fixed red blood cells are prepared leukocyte analogs.

2. The method according to claim 1, wherein the surfactant concentration of the morphology adjusting component is between 0.005%:1.5%.

3. The method according to claim 1, wherein the osmotic regulator is at least one of the following: sodium chloride, monobasic sodium phosphate, potassium chloride and sodium citrate.

4. The method according to claim 1, wherein the treated red blood cells are subjected to fixation with 0.5% glutaraldehyde for about 2 hours.

5. The method according to claim 1, wherein the surfactant is a cationic, anionic, nonionic and/or zwitterionic surfactant, and the morphology adjusting component optionally comprises acetic acid.

6. The method according to claim 1, wherein the surfactant is selected from at least one of the following: sodium dodecyl sulphonate, sodium hexadecyl sulphonate and hexadecyl trimethyl ammonium chloride.

7. The method according to claim 1, wherein the oxidizing agent or reducing agent is selected from at least one of the following: sodium nitrite, potassium dichromate, potassium permanganate, hydrogen peroxide and sodium sulphite.

8. The method according to claim 1, wherein the cell membrane strengthening component is an aldehyde compound selected from at least one of the following: paraformaldehyde, formaldehyde, pyruvaldehyde, oxalaldehyde, glutaraldehyde, and a mixture thereof.

9. The method according to claim 1, wherein the surfactant is selected from the following: 0.005%-0.5% (w/v) sodium dodecyl sulphonate, and 0.005%-0.5% (w/v) hexadecyl trimethyl ammonium chloride, based on the final concentration.

10. The method according to claim 1, wherein the oxidizing agent or reducing agent is selected from the following: 0.1%-1% (w/v) sodium nitrite, 0.1%-2% (w/v) potassium dichromate, 0.05%-2% (w/v) potassium permanganate, 0.05%-5% (v/v) hydrogen peroxide, and 0.1%-2% (w/v) sodium sulphite, based on the final concentration.

11. The method according to claim 1, wherein the osmotic regulator is selected from the following: 0.75-2% (w/v) sodium chloride solution, 1%-3% (w/v) monobasic sodium phosphate solution, 0.75-2% (w/v) potassium chloride solution, and 1%-4% (w/v) sodium citrate solution, based on the final concentration.

12. The method according to claim 1, wherein the cell membrane strengthening component is selected from the following: 0.01%-0.1% (v/v) glutaraldehyde, 0.05%-0.5% (v/v) formaldehyde, 0.05-0.2% (v/v) mixed aldehydes of formaldehyde and glutaraldehyde in a volume ratio of 3:1-40:1, 0.05%-0.5% (v/v) pyruvaldehyde, and 0.01%-0.1% (v/v) paraformaldehyde, based on the final concentration.

* * * * *